(12) United States Patent
Gately et al.

(10) Patent No.: US 7,717,898 B2
(45) Date of Patent: *May 18, 2010

(54) SHIELDED TIP CATHETER

(75) Inventors: Nicholas V. Gately, Lambertville, NJ (US); W. Perry Arnold, Glen Arm, MD (US)

(73) Assignee: Medical Components, Inc., Harleysville, PA (US)

(*) Notice: Subject to any disclaimer, the term of this patent is extended or adjusted under 35 U.S.C. 154(b) by 1066 days.

This patent is subject to a terminal disclaimer.

(21) Appl. No.: 11/268,082

(22) Filed: Nov. 7, 2005

(65) Prior Publication Data

US 2006/0064072 A1   Mar. 23, 2006

Related U.S. Application Data

(63) Continuation of application No. 10/644,238, filed on Aug. 20, 2003, now Pat. No. 6,991,625.

(60) Provisional application No. 60/405,937, filed on Aug. 23, 2002.

(51) Int. Cl.
*A61M 25/00* (2006.01)
*A61M 5/00* (2006.01)

(52) U.S. Cl. ...................... 604/523; 604/264

(58) Field of Classification Search .............. 604/43, 604/264, 525, 523, 534, 538, 93.01, 164.06, 604/173
See application file for complete search history.

(56) References Cited

U.S. PATENT DOCUMENTS

| | | | |
|---|---|---|---|
| 4,134,402 A | 1/1979 | Mahurkar | |
| 4,568,329 A | 2/1986 | Mahurkar | |
| 4,627,436 A * | 12/1986 | Leckrone | 606/7 |
| 4,808,155 A | 2/1989 | Mahurkar | |
| 4,995,865 A | 2/1991 | Gahara et al. | |
| 5,053,023 A | 10/1991 | Martin | |
| 5,167,623 A | 12/1992 | Cianci et al. | |
| 5,197,951 A | 3/1993 | Mahurkar | |
| 5,374,245 A | 12/1994 | Mahurkar | |
| 5,405,320 A | 4/1995 | Twardowsaki et al. | |
| 5,405,341 A * | 4/1995 | Martin | 604/284 |
| 5,509,897 A | 4/1996 | Twardowski et al. | |
| 5,522,807 A | 6/1996 | Luther | |
| 5,554,136 A | 9/1996 | Luther | |
| 5,989,213 A | 11/1999 | Maginot | |
| 6,190,371 B1 | 2/2001 | Maginot et al. | |

(Continued)

*Primary Examiner*—Manuel A Mendez
(74) *Attorney, Agent, or Firm*—Anton P. Ness; Fox Rothschild LLP

(57) ABSTRACT

A multilumen catheter assembly (100) including an elongated body (108) having a proximal end (102) and a distal end (104) and a first lumen (110) having a sidewall (118) extending between the proximal end and the distal end, a first distal opening (151) disposed at the distal end, and a first guide wire opening (152) disposed proximally of the distal end and coplanar with the sidewall. The assembly also includes a second lumen (112) connected to the sidewall and extending from the proximal end toward the distal end, proximally of the distal end. The second lumen (112) includes a second opening (155) extending obliquely away from the sidewall distally toward the first distal opening (114) and a second guide wire opening (155) disposed proximally of the second opening (155) and in a plane generally parallel to the sidewall. A method of inserting the catheter into a vessel is also disclosed.

7 Claims, 4 Drawing Sheets

U.S. PATENT DOCUMENTS

| | | |
|---|---|---|
| 6,280,423 B1 | 8/2001 | Davey et al. |
| 6,409,700 B1 | 6/2002 | Siegel, Jr. et al. |
| 6,595,966 B2 * | 7/2003 | Davey et al. ................ 604/264 |
| 6,966,886 B2 | 11/2005 | Appling |
| 6,991,625 B1 * | 1/2006 | Gately et al. ................ 604/523 |
| 7,141,035 B2 | 11/2006 | Haggstrom |
| 7,182,746 B2 | 2/2007 | Haarala et al. |
| 2004/0167463 A1 * | 8/2004 | Zawacki et al. ............... 604/43 |

* cited by examiner

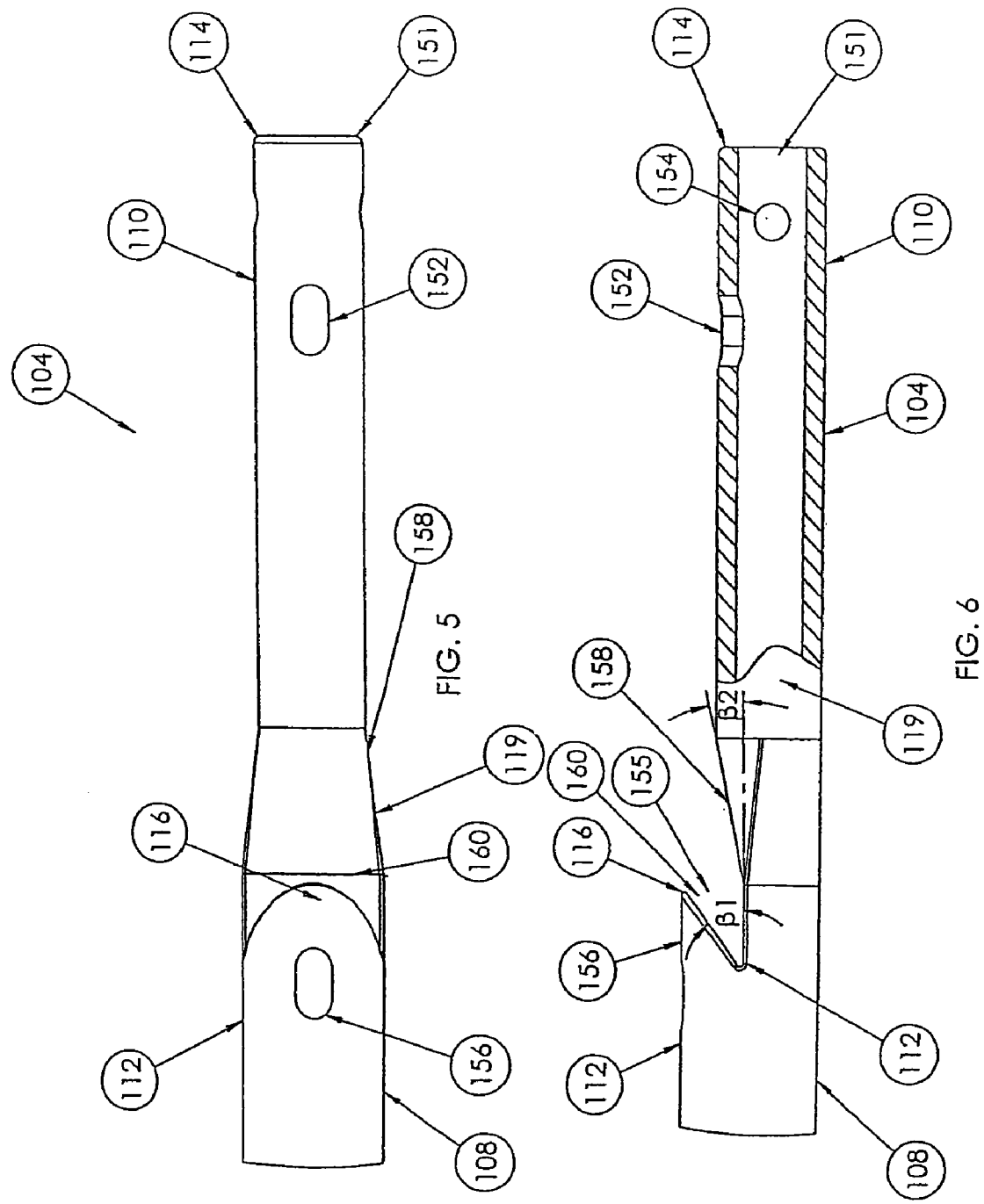

SHIELDED TIP CATHETER

CROSS REFERENCE TO RELATED APPLICATIONS

The present application is a Continuation application of U.S. patent application Ser. No. 10/644,238 filed Aug. 20, 2003 which claims priority from U.S. Provisional Patent Application Ser. No. 60/405,937 filed Aug. 23, 2002.

FIELD OF THE INVENTION

The present invention relates to a multilumen catheter assembly used to simultaneously withdraw and infuse a fluid to a body, such as during hemodialysis.

BACKGROUND OF THE INVENTION

Catheters for the introduction or removal of fluids may be placed in various venous locations and cavities throughout the body for introduction or removal of these fluids. Such catheterization may be performed by using a single catheter assembly having multiple lumens. A typical example of a multiple lumen catheter assembly is a dual lumen catheter in which one lumen introduces fluid and the other lumen removes fluid. Such a multiple lumen catheter assembly is known as the SPLIT STREAM™ catheter, manufactured and sold by Medical Components, Inc. of Harleysville, Pa.

Generally, to insert any catheter into a blood vessel, the vessel is identified by aspiration through a long hollow needle in accordance with the well known Seldinger technique. When blood enters a syringe attached to the needle, indicating that the vessel has been found, a thin guide wire is then introduced, typically through the puncturing needle or other introducer device into the lumen of the vessel. The introducer device is then removed, leaving the guide wire within the vessel. The guide wire projects beyond the surface of the skin. At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire, for example, for insertion of small diameter dual lumen catheters. If the catheter to be inserted is significantly larger than the guide wire, a dilator device is passed over the guide wire to enlarge the opening into the vessel and then removed. The catheter is then passed over the guide wire, and the guide wire is then removed, leaving the catheter within the vessel.

During hemodialysis, the two lumens, the arterial lumen and the venous lumen, are connected to a hemodialysis machine and are used to remove toxic blood from the patient for dialysis and to return dialyzed blood to the patient, respectively. However, suction of the toxic blood into the arterial lumen may draw the distal opening of the arterial lumen against the wall of the blood vessel into which the lumen is inserted, reducing or cutting off blood flow through the arterial lumen, and significantly reducing the amount of blood being dialyzed. This reduction in blood flow can lead to a longer dialysis period, or result in less dialysis of the patient's blood. It would be beneficial to provide a catheter that reduces the suction of the arterial lumen against the blood vessel wall.

Twardowski et al., U.S. Pat. No. 5,405,320 and Davey et al., U.S. Pat. No. 6,280,423 B1 both disclose dual lumen catheters with an arterial lumen that includes an overhanging lip or shield to reduce the suction of the arterial lumen against the blood vessel wall. However, neither Twardowski et al. nor Davey et al. disclose a structure or method for inserting the catheter into the blood vessel that minimizes the likelihood of the overhanging lip snagging on the blood vessel wall during insertion. It would be beneficial to provide a catheter having an overhanging lip and a method of inserting the catheter that minimizes the likelihood of such snagging.

BRIEF SUMMARY OF THE INVENTION

Briefly, the present invention provides a multilumen catheter assembly. The assembly includes an elongated tubular body, divided by a sidewall extending throughout the center of the tube, dividing the tube into two generally "D-shaped" lumens, of which the distal openings are at unequal lengths. The most distal tip is round and non-tapered with an oval side opening just proximal to the distal opening to facilitate guide wire passage. The shorter, more proximal undercut lip lumen has a single oval side hole opening directly centered just proximal to the center of the undercut (overhanging) lip. The two oval side holes facilitate passage of a guide wire for insertion. The shorter lumen (the arterial or aspiration port) connects through a connecting hub assembly to allow oblique connection of an arterial (generally red color coded) port luer-lock connection tube. The longer lumen (the venous or return port) connection in the hub assembly in a straight-through direction for connection to the venous (generally blue color coded) luer-lock connection tube.

Additionally, the present invention provides a method of inserting a catheter assembly over a catheter guide wire. The proximal end of the guide wire is inserted into the tip of the longer (venous return) lumen, out the oval guide wire side hole parallel to the lumen and enters the shorter (arterial aspiration) lumen through the oval guide wire hole into the lumen of the aspiration port. The guide wire is then advanced through the length of the catheter to exit the red luer-lock connector. The catheter is then advanced over the guide wire for percutaneous insertion without a peel away sheath, thus minimizing the possibility of bleeding and air embolism. The course of the guide wire through the catheter tips allows an insertion course co-axial to the guide wire and provides that the overhanging undercut lip of the shorter port is folded down against the longer venous port to prevent difficult passage as the catheter passes through the venotomy site.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 5 is an enlarged top plan view of the distal end of the catheter assembly shown in FIG. 1.

FIG. 6 is an enlarged side view of the distal end of the catheter assembly shown in FIG. 1.

DETAILED DESCRIPTION OF THE INVENTION

Figure 1:
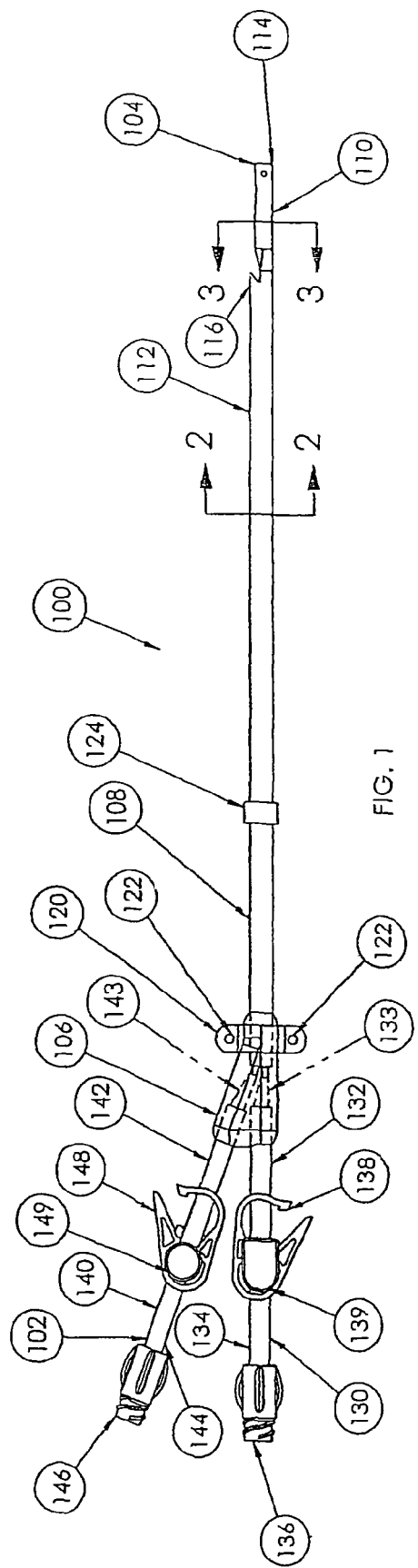
FIG. 1 is a side view of a catheter assembly according to a preferred embodiment of the present invention.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of the catheter according to the present invention. The terminology includes the words above specifically mentioned, derivatives thereof, and words of similar import. The following describes preferred embodiments of the invention. However, it should be understood based on this disclosure, that the invention is not limited by the preferred embodiments described herein.

Referring now to FIG. 1, a side view of a catheter assembly 100 according to a preferred embodiment of the present invention is shown. The catheter assembly 100 includes a proximal end 102, a distal end 104, and a hub 106 connecting the proximal end 102 and the distal end 104. An elongated body 108 extends between the hub 106 and the distal end 104. The elongated body 108 is preferably comprised of a first catheter lumen 110, also known as a venous lumen and a second catheter lumen 112, also known as an arterial lumen. While only two catheter lumens 110, 112 are shown, those skilled in the art will recognize that the catheter assembly 100 may include more than two lumens 110, 112.

Figure 2:
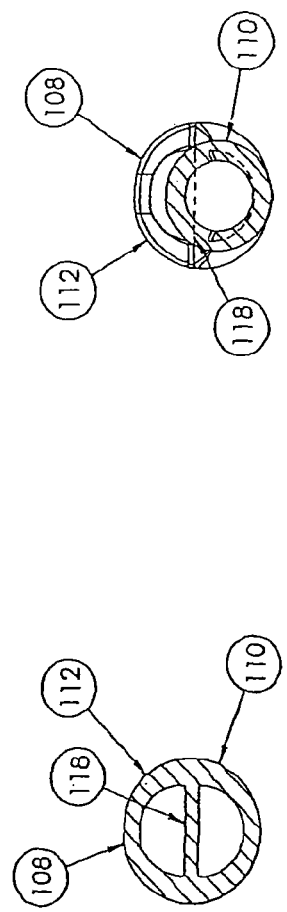
FIG. 2 is an enlarged cross sectional view of the catheter lumens shown in FIG. 1, taken along lines 2-2 of FIG. 1.
Figure 3:
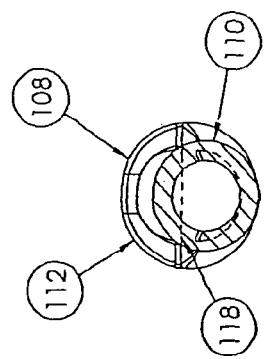
FIG. 3 is an enlarged cross sectional view of the catheter lumens shown in FIG. 1, taken along lines 3-3 of FIG. 1.

The first lumen 110 extends all of the way between the hub 106 and the distal end 104 and terminates at the distal end 104 in a first distal tip 114, while the second lumen 112 begins at the hub 106, but terminates prior to the distal end 104 at a second distal tip 116. FIG. 2 shows an enlarged sectional view of the first and second lumens 110, 112 proximate of the second distal tip 116. A common sidewall 118 extends from the hub 106 and terminates at the second distal tip 116. FIG. 3 shows an enlarged sectional view of the first lumen 110 distal of the second distal tip 116.

Referring back to FIG. 2, the catheter body 108 preferably has a generally circular cross section, with the first lumen 110 and the second lumen 112 each having a generally "D-shaped" cross section, juxtaposed from each other across the common sidewall 118. Although the cross section of the body 108 is preferably circular, those skilled in the art will recognize that the cross section of the body 108 may be other shapes, such as oval. It is preferred that the cross section of the body 108 be a generally smooth curve to facilitate sealing of the patient's skin around the body 108 at the incision site, as well as at the entrance to the vessel, to minimize bleeding. Distal of the second distal tip 116, the first lumen 110 preferably has a generally circular cross section.

Figure 4:
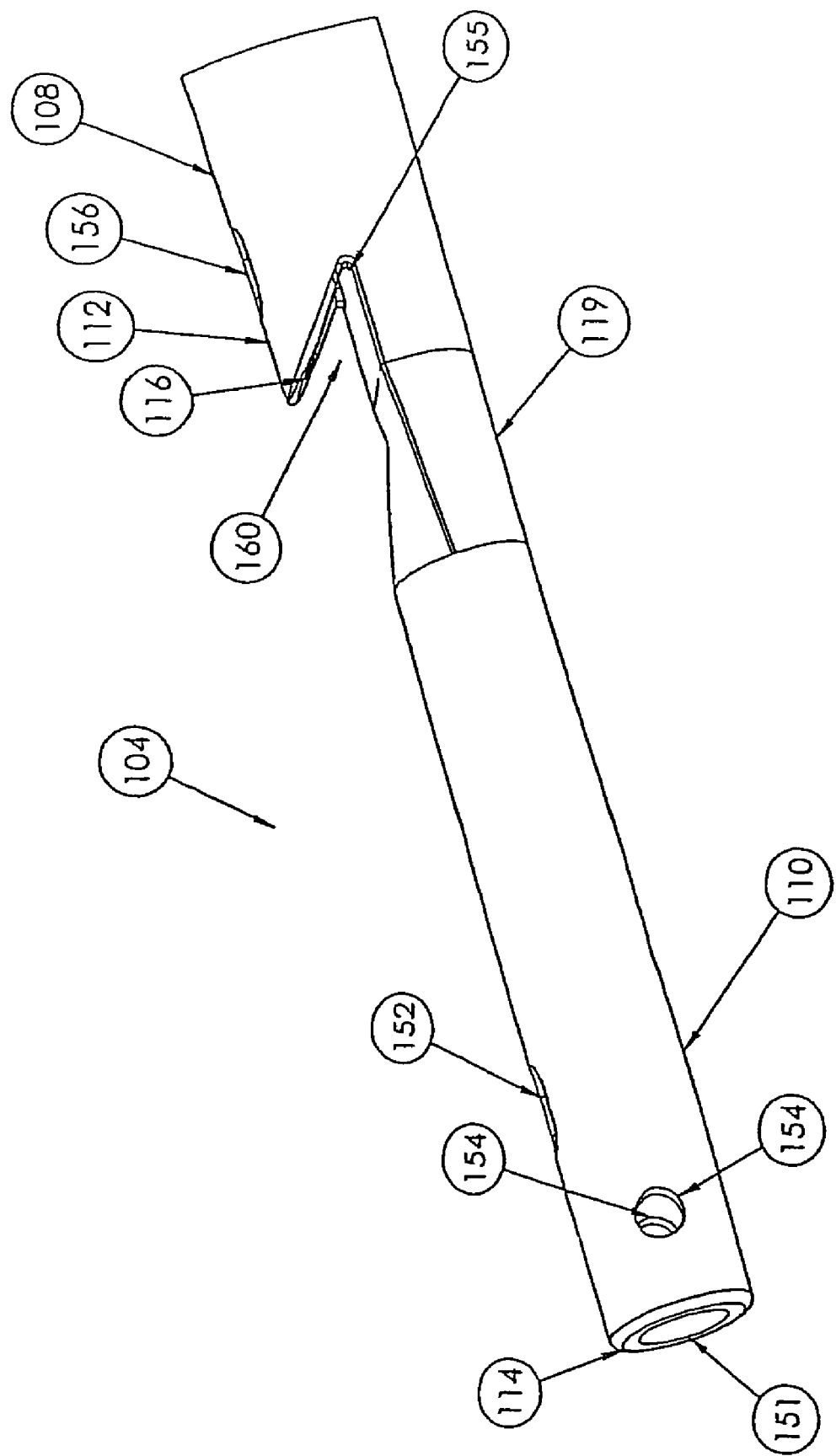
FIG. 4 is an enlarged perspective view of a distal end of the catheter assembly shown in FIG. 1.

FIGS. 4, 5, and 6 show an enlarged perspective view, an enlarged top plan view and an enlarged side view, respectively, of the distal end 104 of the catheter assembly 100. A transition portion 119 of the first lumen 110 disposed between the first distal tip and the second distal tip transitions the cross-section of the first lumen 110 from the D-shape shown in FIG. 2 to the generally circular cross section shape shown in FIG. 3.

Preferably, the body 108 is constructed from a polymer or elastomer, such as CARBOTHANE® polyurethane, with an approximately 20% barium sulfate/PELLETHANE® polyurethane composition to aid in locating the body 108 within the patient's vessel after insertion, such as by ultrasound and fluoroscopy. However, those skilled in the art will recognize that other biocompatible materials may be used for the body 108. Preferably, the body 108 has a hardness of approximately 80-A on the Shore durometer scale, although those skilled in the art will recognize that the body 108 may be harder or softer.

Referring back to FIG. 1, the hub 106 preferably includes a suture wing 120 that extends generally transverse of the body 108. The suture wing 120 preferably includes at least one and, more preferably, at least two suture openings 122 that allow an inserting physician to suture the hub 106 to the external skin of the patient into whom the physician has inserted the catheter assembly 100 to prevent the catheter assembly 100 from being dislodged from its inserted position within the patient. The suture wing 120 may be fixedly connected to the hub 106, or the suture wing 120 may be rotatably connected to the hub 106, to allow the suture wing 120 to rotate about the hub 106, allowing the inserting physician additional flexibility in positioning the hub 106 relative to the skin of the patient.

Preferably, a catheter tissue ingrowth cuff 124 is disposed along an exterior of the body 108 between the second distal tip 116 and the hub 106. The catheter tissue ingrowth cuff 124 is used for chronic catheter insertions, wherein the catheter assembly 100 is intended to be inserted into the patient for extended periods of time, such as for several months. The catheter tissue ingrowth cuff 124 is disposed within a subcutaneous tunnel according to methods known by those skilled in the art. Preferably, the catheter tissue ingrowth cuff 124 is constructed from a generally coarse fabric material, such as a polyester or DACRON® polyester, to enable ingrowing subcutaneous/skin tissue to engage the material and secure the catheter ingrowth cuff 124 to the subcutaneous/skin tissue. For an acute catheterization, the catheter assembly 100 need not be subcutaneously tunneled, and the catheter ingrowth cuff 124 may be omitted.

The proximal end 102 of the catheter assembly 100 includes a first extension tube 130 that fluidly communicates with the first lumen 110 at a distal end 132 of the first extension tube through a first hub conduit 133. The first hub conduit 133 transitions from a generally circular cross section at the first extension tube 130 to a generally D-shaped cross section at the first lumen 110. The proximal end 102 of the catheter assembly 100 also includes a second extension tube 140 that fluidly communicates with the second lumen 112 at a distal end 142 of the second extension tube 140 through a second hub conduit 143. The second hub conduit 143 transitions from a generally circular cross section at the second extension tube 140 to a generally D-shaped cross section at the second lumen 112. Preferably, the first extension tube 130 extends generally co-axially with the first lumen 110 and the second extension tube 140 extends at an angle of approximately 20 degrees relative to the length of the second lumen 112, although those skilled in the art will recognize that the first and second extension tubes 130, 140 may extend at other angles as well. Preferably, each of the first and second extension tubes 130, 140 is constructed from PELLETHANE® polyurethane, although those skilled in the art will recognize that other material may be used. A proximal end 134 of the first extension tube 130 preferably terminates at a first connector 136, such as a standard luer lock, as is well known in the art. Preferably, the first connector 136 is color coded blue to indicate connection to the venous lumen 110. Also, a proximal end 144 of the second extension tube 140 preferably terminates at a second connector 146, such as a standard luer lock. Preferably, the second connector 146 is color coded red to indicate connection to the arterial lumen 112.

A first clamp 138, such as a Roberts clamp is preferably disposed over the first extension tube 130 between the proximal end 134 and the distal end 132 of the first extension tube 130, and a second clamp 148 is preferably disposed over the second extension tube 140 between the proximal end 144 and the distal end 142 of the second extension tube 140. The first and second clamps 138, 148 serve to releasably secure each of the first and second extension tubes 130, 140, respectively, preventing fluid flow through each of the first and second extension tubes 130, 140 when the respective clamp 138, 148 is in the closed position.

An information ring 139, 149 is disposed within each respective clamp 138, 148. An example of such an information ring 139, 149 is disclosed in either of U.S. Pat. No. 6,823,617 or U.S. Design Pat. No. D489,452, which are both owned by the assignee of the present invention, and which are both incorporated herein by reference in their entireties. Indicia, such as manufacturer's logo, lumen priming volume, warnings, or other indicia, may be printed on each information ring 139, 149.

Referring back to FIGS. 4-6, the distal end 104 of the catheter assembly 100 is now described in more detail. The first lumen 110 preferably includes a generally circular first distal opening 151 disposed at the first distal tip 114 and a first guide wire opening 152 that is disposed proximally of the first distal tip 114. Preferably, the first guide wire opening 152 is generally oblong or oval in shape, with a major axis of the first guide wire opening 152 extending parallel to a major axis of the body 108. The first guide wire opening 152 is preferably generally parallel to a plane of the sidewall 118. Further, the first lumen 110 preferably includes at least one and, more preferably, a plurality of first side ports 154, each being disposed in a plane generally perpendicular to the plane of the sidewall 118. Preferably, each of the plurality of first side ports 154 is generally circular, although those skilled in the art will recognize that the first side ports 154 may be other shapes. Preferably, the first distal tip 114 includes a generally circular bevel to facilitate a smooth transition between the first distal tip 114 and the body of the first lumen 110, and to reduce the risk of the first distal tip 114 snagging the wall of the blood vessel during insertion.

The second distal tip 116 of the second lumen 112 is generally parabolic in shape and extends obliquely away from the sidewall 118 distally toward the first distal opening 151. The generally parabolic shape of the second distal tip 116 forms an overhanging lip, as seen in FIGS. 1, 4, and 6. Referring to FIG. 6 only, preferably, the second distal tip 116 of the second lumen 112 extends at an angle β1 of approximately 37.5 degrees relative to the plane of the sidewall 118, although those skilled in the art will recognize that the angle β1 may be other than 37.5 degrees.

Referring to FIGS. 4 and 6, the second distal tip 116 preferably includes a second distal opening 155 and a second guide wire opening 156 that is disposed proximally of the second distal opening 155. Preferably, the second guide wire opening 156 is generally oblong or oval in shape, with a major axis of the second guide wire opening 156 extending parallel to a major axis of the body 108.

The transition portion 119 preferably includes a tapered wall 158 that angles at an angle β2 of approximately 30 degrees from the plane of the sidewall 118. A cavity 160 is formed between the tapered wall 158 and the second distal tip 116. The cavity 160 and the oblique shape of the second distal tip 116 assist in blood flow into the second lumen 112 through the second distal tip opening 155 during hemodialysis, as will be described in more detail later herein.

To insert the catheter assembly 100 into the patient, an incision is initially made near an insertion site on the patient's skin, which is to be aspirated with a syringe or other introducer apparatus near or proximate the area to be catheterized. If the catheter assembly 100 is used for hemodialysis and the area to be catheterized is the internal jugular vein, the incision is made in the clavicular triangle region. The exact location of the incision can be varied by the physician. In accordance with the Seldinger technique, a hollow needle is inserted through the incision and into the vein, and the vein is then aspirated. A guide wire is then passed through the needle and the needle is removed. Next, after dilating the soft tissue track and venatory site, the catheter assembly 100 is inserted over the guide wire. This insertion technique eliminates the need for a sheath to be inserted over the guide wire, greatly reducing the risk of air embolism.

Figure 7:
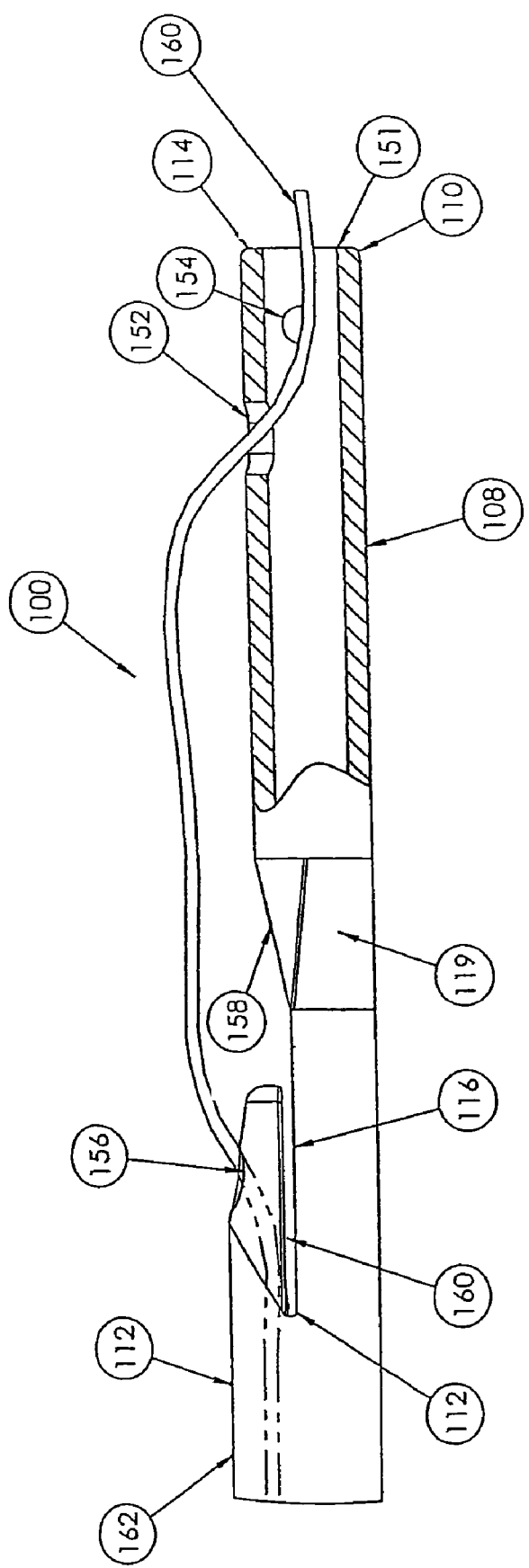
FIG. 7 is an enlarged side view of the distal end of the catheter assembly shown in FIG. 1, with a guide wire strung through the distal end of the catheter assembly as during insertion of the catheter assembly.

Prior to insertion of the catheter assembly 100 into the patient, the catheter assembly 100 of FIG. 1 is inserted over the proximal end of the guide wire as follows. A proximal end 162 of a guide wire 160, shown in FIG. 7, is inserted into the first distal opening 151 and pushed through the first lumen 110 to the first guide wire opening 152. The proximal end 162 of the guide wire 160 is then pushed through the first guide wire opening 152, so that the proximal end 162 of the guide wire 160 exits the catheter body 108. The proximal end 162 of the guide wire 160 is next pulled longitudinally along the exterior of the first lumen 110 and over the second distal tip 116 to the second guide wire opening 156, where the proximal end 162 of the guide wire 160 is inserted through the second guide wire opening 156 and into the second lumen 112. The proximal end 162 of the guide wire 160 is inserted through the second lumen 112 and pushed through the second lumen 112 until the proximal end 162 of the guide wire 160 exits the catheter assembly 100.

As the guide wire 160 is pulled through both the first guide wire opening 152 and the second guide wire opening 156, the guide wire 160 between the first guide wire opening 152 and the second guide wire opening 156 engages the second distal tip 116 and directs the second distal tip 116 into the cavity 160, as shown in FIG. 7. With the second distal tip 116 in this position, the distal end 104 of the catheter assembly 100 may be inserted into the vessel more directly, preventing the second distal tip 116 from catching on the wall of the blood vessel and potentially snagging on the wall of the vessel. The distal end 104 of the catheter assembly 100 is inserted as far into the vessel as desired by the physician, and as confirmed by fluoroscopy. When the distal end 104 of the catheter 100 is in its desired position, the guide wire 160 is pulled through the proximal end 102 of the catheter assembly 100 and removed. Next, the incision is closed and the hub 106 is secured to the external skin of the patient by suturing the suture wing 120 to the skin. The open of first and second connectors 136, 146 are connected in fluid communication to respective fluid inlets and outlets of a hemodialysis unit (not shown), or other fluid transfer equipment (not shown) and dialysis may now begin.

In use, after the dialysis machine is connected to the catheter assembly 100 and turned on, the dialysis machine draws blood from the vessel through the second lumen 112. In the event that the pressure drop in the vessel caused by the blood being drawn into the second lumen 112 forces the wall of the vessel toward the second distal opening 155, the overhanging lip of the second distal tip 116 prevents the vessel wall from totally occluding the second distal opening 155 and shutting off blood flow through the second lumen 112.

The blood drawn into the second lumen 112 flows to the hemodialysis machine where the blood is cleaned and processed. The blood is then pumped through the first lumen 110 for discharge back into the vessel. The first distal opening 151 and the first side ports 154 provide discharge ports for the blood to be discharged from the first lumen 110.

Figure 8:
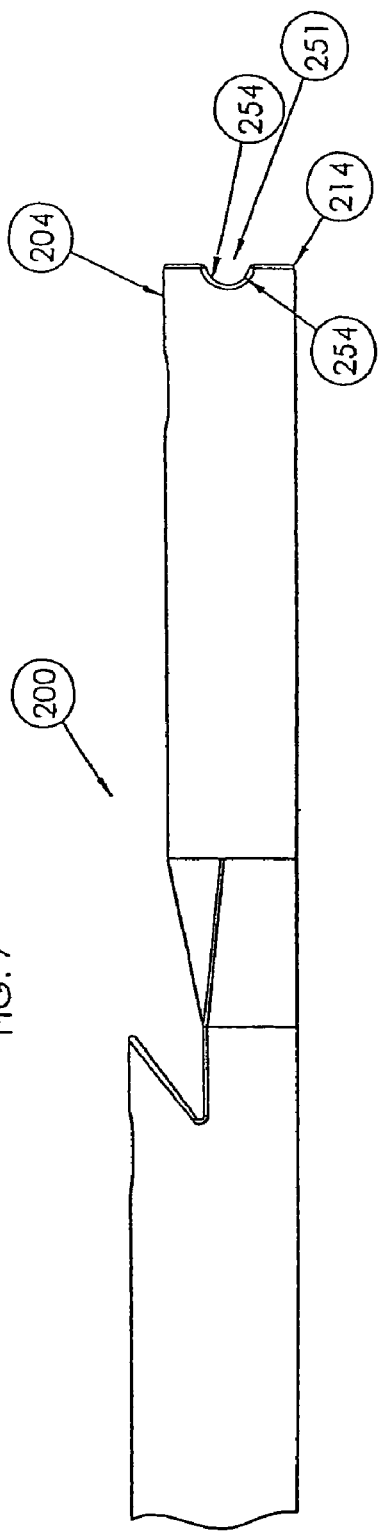
FIG. 8 is an enlarged side view of a distal end of an alternate embodiment of a catheter assembly according to an alternative embodiment of the present invention.

A distal end 204 of an alternate embodiment of a catheter assembly 200 having an alternate first distal tip 214 is shown in FIG. 8. Instead of a plurality of generally circular side ports 154 as shown in the first distal tip 114 of the embodiment in FIG. 4, the alternate first distal tip 214 includes a plurality of side ports 254 that are each generally semi-circular and end at the most distal portion of the first distal tip 214, merging with the first distal opening 251.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A multilumen catheter assembly comprising:
   an elongated body having a proximal end and a distal end;
   a first lumen extending between the proximal end and the distal end, and having a first distal opening disposed at the distal end;
   a second lumen and extending between the proximal end and a second distal end, proximal of the distal end,
   a sidewall extending between the proximal end and the distal end and separating the first and second lumens,
   wherein the second lumen includes a second opening extending obliquely away from the sidewall distally toward the first opening; and
   wherein the second distal end concludes in a tip section that is undercut along the sidewall from a first side of the elongated body to a second, opposite side thereof to form an overhanging lip, thereby facilitating prevention of occlusion of the second opening by the vessel wall.

2. The multilumen catheter assembly according to claim 1, wherein the undercut beneath the second distal end tip section is elongated.

3. The multilumen catheter assembly according to claim 1, wherein the second distal end tip section is elongated to enable deflection toward the first lumen during patient insertion.

4. The multilumen catheter assembly according to claim 3, wherein the second distal end tip section is tapered and includes a sidewall portion facing away from the first lumen that is angled slightly distally.

5. The multilumen catheter assembly according to claim 3, wherein the first lumen, distally of the second lumen distal tip section, includes a transition portion that transitions the cross-section of the first lumen from a generally noncircular cross section shape to a generally circular cross section shape, and includes a tapered wall angled slightly proximally toward the second lumen distal tip section.

6. The multilumen catheter assembly according to claim 1, wherein the first lumen and the second lumen each have a cross-sectional area sufficiently large in cross-sectional area for blood transmission therethrough.

7. The multilumen catheter assembly according to claim 1, wherein at least the second lumen has a cross section that is D-shaped.

* * * * *